United States Patent
Haefliger et al.

(12)

(10) Patent No.: US 6,251,406 B1
(45) Date of Patent: Jun. 26, 2001

(54) ATTENUATED MICROORGANISM STRAINS AND THEIR USES

(75) Inventors: Denise N. Haefliger, Lausanne; Jean-Pierre Kraehenbuhl, Rivaz, both of (CH)

(73) Assignee: BTG International Limited, London (GB)

(*) Notice: Subject to any disclaimer, the term of this patent is extended or adjusted under 35 U.S.C. 154(b) by 0 days.

(21) Appl. No.: 09/413,807

(22) Filed: Oct. 7, 1999

Related U.S. Application Data (62) Division of application No. 09/288,861, filed on Apr. 9, 1999, and a continuation of application No. PCT/GB97/02740, filed on Oct. 7, 1997.

(30) Foreign Application Priority Data

Oct. 9, 1996 (GB) .................................... 9621091

(51) Int. Cl.$^7$ .................................... A61K 39/112
(52) U.S. Cl. .................. 424/258.1; 424/204.1; 424/192.1; 424/234.1; 424/93.1; 424/93.2; 435/5; 435/7.1; 435/235.1; 435/320.1
(58) Field of Search .............. 424/204.1, 192.1, 424/234.1, 258.1, 93.1, 93.2; 435/5, 7.1, 235.1, 320.1; 536/23.72

(56) References Cited

U.S. PATENT DOCUMENTS

| | | |
|---|---|---|
| 5,411,857 | 5/1995 | Beaudenon et al. . |
| 5,447,839 | 9/1995 | Manos et al. . |
| 5,618,536 | 4/1997 | Lowy et al. . |
| 5,665,533 | 9/1997 | Hopfl et al. . |
| 5,665,571 | 9/1997 | Beaudenon et al. . |
| 5,709,996 | 1/1998 | Lowy et al. . |
| 5,712,092 | 1/1998 | Orth et al. . |
| 5,716,620 | 2/1998 | Lowy et al. . |
| 5,738,853 | 4/1998 | Ludmerer et al. . |
| 5,744,142 | 4/1998 | Lowy et al. . |
| 5,756,284 | 5/1998 | Lowy et al. . |
| 5,795,754 | 8/1998 | Ludmerer et al. . |
| 5,821,087 | 10/1998 | Lowe et al. . |

FOREIGN PATENT DOCUMENTS

| | | |
|---|---|---|
| 451550 | 10/1991 | (EP) . |
| 256321 | 2/1998 | (EP) . |
| 83/03623 | 10/1983 | (WO) . |
| 86/05816 | 10/1986 | (WO) . |
| 87/01375 | 3/1987 | (WO) . |
| 90/04790 | 5/1990 | (WO) . |
| 90/10867 | 9/1990 | (WO) . |
| 91/18118 | 11/1991 | (WO) . |
| 91/18294 | 11/1991 | (WO) . |
| WO 92 08486 | 5/1992 | (WO) . |
| 92/11369 | 7/1992 | (WO) . |
| 93/00436 | 1/1993 | (WO) . |
| 93/02184 | 2/1993 | (WO) . |
| 94/00152 | 1/1994 | (WO) . |
| WO 94 03615 | 2/1994 | (WO) . |
| 94/05792 | 3/1994 | (WO) . |
| 94/20621 | 9/1994 | (WO) . |
| 94/23037 | 10/1994 | (WO) . |
| 95/01374 | 1/1995 | (WO) . |
| 95/20659 | 8/1995 | (WO) . |
| 95/31476 | 11/1995 | (WO) . |
| 95/31532 | 11/1995 | (WO) . |
| 96/09375 | 3/1996 | (WO) . |
| 96/11272 | 4/1996 | (WO) . |
| 96/11273 | 4/1996 | (WO) . |
| WO 96 11274 | 4/1996 | (WO) . |
| 96/15247 | 5/1996 | (WO) . |
| 96/26277 | 8/1996 | (WO) . |
| 96/29413 | 9/1996 | (WO) . |
| 96/30520 | 10/1996 | (WO) . |
| 97/46693 | 12/1997 | (WO) . |
| 98/19790 | 5/1998 | (WO) . |
| 98/28003 | 7/1998 | (WO) . |
| 98/42847 | 10/1998 | (WO) . |

OTHER PUBLICATIONS

Fouts et al . Vaccine, 1995, vol. 17, pp. 1697–1705.*

Kirnbauer et al . J of Virology, 1993, pp. 6929–6936.*

Londono et al . Vaccine, 1996, vol. 14, pp. 545–552.*

Hopkins et al . Infection And Immunity, 1995, pp. 3279–3286.*

Banks et al . J General Virology, 1987, vol. 68, pp. 3081–3089.*

Galloway, "Is vaccination against human papillomavirus a possibility?" The Lancet, vol. 351, pp. sm22–24 (1998); and Vaccine, vol. 12, No. 1, p. 91 "Recombinant papillomavirus capside protein; . . . " (1994).

Sapp et al, "Synthesis, Properties and Applications . . . ", Intervirology, vol. 39, pp. 49–53 (1996).

Krul M.R.L. et al.: "Induction of an antibody response in mice against human papillomavirus (HPV) type 16 after immunization with HPV recombinant Salmonella strains." Cancer Immunol. Immunother., vol. 43, Sep. 1996, pp. 44–48, XP002054899 see the whole document.

(List continued on next page.)

Primary Examiner—Ali R. Salimi
(74) Attorney, Agent, or Firm—Nixon & Vanderhye (57) ABSTRACT

This application relates to the use of attenuated prokaryotic miccrooganism strains (such as Salmonella) expressing nucleic acid encoding HPV proteins as vaccines against HPV infection and he associated increased risk of cancer. In particular, the work shows that it is possible to assemble VLPs in a prokaryotic organism and that nasal immunization of mice with the strains HPV-specific conformationally dependent and neutralizing antibodies in serum and genital secretions. The experiments described herein show that it is also possible to assemble chimeric VLPs of a HPV including a fusion partner and that tumor protection can be induced.

16 Claims, 8 Drawing Sheets

OTHER PUBLICATIONS

Hormaeche C.E. et al.: Salmonella Vaccines: Mechanisms of immunity and their use as carriers of recombinant antigens.: 1995, John Wiley & Sons Ltd., Chichester, UK; pp. 119–153; XP002054901 see p. 129—p. 140.

Nardelli–Haefliger D. et al.: "Human papillomavirus type 16 virus–like particles expressed in attenuated *Salmonella typhimurium* elicit mucosal and systemic neutralizing antibodies in mice." Infectiona and Immunity, vol. 65, No. 8, Aug. 1997, pp. 3328–3336, XP002054900 see the whole document.

Kirnbauer et al, "Papillomavirus L1 major capsid protein," Proc. Natl. Acad. Sci. USA, vol. 89, pp. 12180–12184 (1992).

Zhang et al, "Expression of Human Papillomavirus Type . . . ," Virology, vol. 243, pp. 423–431 (1998).

Zhou et al, "Increased antibody responses to human papillomavirus . . . ," Journal of General Virology, vol. 71, pp. 2185–2190 (1990).

Cason et al, "Towards vaccines against human . . . ," Vaccine, vol. 11, Issue 6, pp. 603–611 (1993).

Rose et al, "Expression of Human Papillomavirus Type 11 . . . ," Journal of Virology, Apr. 1993, p. 1936–1944.

Zhou et al, "Increased antibody responses to human . . . ," Journal of General Virology, vol. 71, pp. 2185–2190 (1990).

Kirnbauer et al, "Papillomavirus L1 major capsid . . . ," Proc. Natl. Acad. Sci. USA, vol. 89, pp. 12180–12184 (1992).

Cason et al, "Towards vaccines against human . . . ," Vaccine, vol. 11, Issue 6, pp. 603–611 (1993).

Rose et al, "Expression of Human Papillomavirus . . . ," Journal of Virology, p. 1936–1944 (1993).

Sapp et al, "Synthesis, Properties and Applications of . . . ," Intervirology, vol. 39, pp. 49–53 (1996).

Abstract, 16th International Papillomavirus Conference, Siena, Sep. 5–12 (1997).

* cited by examiner

Plasmid Name: pYA3342
Plasmid Size: 2.77 kb

Comments: *Salmonella* Asd + vector containing the SD and the ORF of *asd* gene without the promoter. Contains a pBR *ori* and complements Δ*asd*.

Fig.10

```
                              SEQUENCE LISTING

<160> NUMBER OF SEQ ID NOS:  2

<210> SEQ ID NO 1
<211> LENGTH: 29
<212> TYPE: DNA
<213> ORGANISM: Human papillomavirus type 16
<220> FEATURE:
<221> NAME/KEY: misc_feature
<222> LOCATION: (1)..(29)
<223> OTHER INFORMATION: HPV16-L1 primer

<400> SEQUENCE: 1
gggccatggc tctttggctg ccttagtga                                       29

<210> SEQ ID NO 2
<211> LENGTH: 26
<212> TYPE: DNA
<213> ORGANISM: Human papillomavirus type 16
<220> FEATURE:
<221> NAME/KEY: misc_feature
<222> LOCATION: (1)..(26)
<223> OTHER INFORMATION: HPV16-L1 primer
```

```
<400> SEQUENCE: 2
gggaagcttc aatacttaag cttacg                                                  26
```

ATTENUATED MICROORGANISM STRAINS AND THEIR USES

This application is a continuation-in part of application Ser. No. 09/288,861, filed Apr. 9, 1999, the entire content of which is hereby incorporated by reference in this application.

This is a continuation of PCT application No. PCT/GB97/02740, filed Oct. 7, 1997, the entire content of which is hereby incorporated by reference in this application.

FIELD OF THE INVENTION

The present invention relates to attenuated strains of prokaryotic microorganisms, in particular Salmonella, transformed with nucleic acid encoding papillomavirus virus proteins, to compositions comprising these microorganisms, especially for use as vaccines, and to the medical uses of these strains. In a further aspect, the present invention provides a method of producing assembled papillomaavirus Virus like particles (VLPs).

BACKGROUND OF THE INVENTION

Human papilloma virus (HPV) 16 is the major type of HPV which, in association with cofactors, can lead to cervical cancer (49). Studies on HPV have been hampered by the inability to propagate the virus in culture, the lack of animal models and the paucity of virions in clinical lesions. This has led to the development of alternative approaches of antigen production for immunological studies. The conformational dependency of neutralizing epitopes, as observed in experimental animal papillomavirus systems (8, 22) suggests that properly assembled HPV particles are critical for the induction and detection of clinically relevant immune reactivity.

The HPV capsids are formed by 72 pentameric capsomers of L1 proteins arranged on a T7 icosahedral lattice (15). Recently, a number of investigators have demonstrated the production of HPV capsids, i.e. virus like particles (VLP), by utilizing baculovirus, vaccinia virus or yeast expression systems (15,22,45,48,61). The potential of VLPs as subunit vaccines has been demonstrated using the cottontail rabbit papillomavirus (CRPV) (4), the canine oral papillomavirus (COPV) (57), and the HPV11 models (45).

HPV16 infects through the genital mucosa, where benign proliferative lesions are confined. Protection against infection with such a pathogen could be provided by specific (anti-VLP) secretory immunoglobulin A (sIgA) or immunoglobulins G (IgG) in genital secretions. By analogy with existing animal models. HPV16 VLPs-specific antibodies in cervical secretions might help to prevent sexually transmitted infection by HPV16 in women. However, this cannot be formally proven in the absence of an experimental model for genital PV infection and other scenarios requiring cell-mediated immunity cannot be excluded.

Moreover, the mechanism underlying HPV infection is unclear. HPV may directly infect the basal cells of the stratified cervical epithelium at the occurrence of breaches. Alternatively, HPV infection could also occur either directly through Langerhans cells in intact epithelia or indirectly from an HPV-producing keratinocyte, and thus neutralizing antibodies will not be functional as shown for other viruses. This further adds to the difficulty in providing vaccines effective against HPV infection.

Immunosuppressed individuals are more prone to develop cervical carcinoma as compared to immuncocompetent individuals, suggesting the possibility of using immunotherapy. Therapeutic vaccines (87) aimed to the treatment of established HPV infection or HPV associated premalignant and malignant lesions have been investigated during the last ten years (59). Evidence for HPV-antigen-directed immunotherapy against cervical cancer comes from the observations that experimental (13),(34),(83) and natural (82) PV-associated tumours can be controlled by immunization with E6 and E7 preparations. These studies suggested that CTL might be the most effective immunological effector mechanisms. E6 and E7 preparations consisted in either peptides (13), bacterially prepared fusion proteins (82), eukaryotic transfected cells (83) or recombinant vaccinia viruses (34).

Recently, chimeric VLPs carrying the 17kD E7 protein as a fusion with L2 have been shown to induce rejection of syngeneic tumour cells (84) engineered to express L1 and/or E7 ORF (i.e. C3 cells (13) and TC1 cells (85)). This data demonstrates the possibility of providing prophylactic and therapeutic effects in the same vaccine preparation. Salmonella that are attenuated, yet invasive, have been proposed for the delivery of heterologous antigens to the mucosal and systemic immune systems (10). The antigen is delivered by the live Salmonella to mucosal inductive sites, where after priming, antigen-specific B and T cells migrate from the site of induction and mature into effector cells. The migrating IgA-expressing B cells home to different mucosal sites, including the genital tract where they differentiate into IgA secreting plasma cells (32). Thus, oral or nasal immunization can provide protective antibodies in genital secretions Recently, we and others have shown that mucosal immunization with recombinant Salmonella can elicit antibody responses in the genital mucosa of mice and humans (18, 37,56).

SUMMARY OF THE INVENTION

In order to develop a prophylactic vaccine against HPV, we have expressed the major protein L1 of HPV16 in a PhoP$^c$ (35) attenuated strain of *Salmonella typhimurium*. Surprisingly, the inventors found for the first time that it is possible to assemble VLPs in a prokaryotic organism and that nasal immunization of mice with an HPV16-L1/Salmonella recombinant strain induces HPV16-specific conformationally dependent and neutralizing antibodies in serum and genital secretions. The experiments described herein also show that it is possible to assemble chimeric VLPs of a HPV protein and a fusion partner.

Accordingly, in a first aspect the present invention provides an attenuated strain of a prokaryotic microorganism transformed with nucleic acid encoding papillomavirus virus major capsid protein wherein the protein assembles in the microorganism to form virus like particles (VLPs).

Thus, the present invention provides a way of producing properly assembled papillomavirus VLPs in an attenuated strain of a prokaryotic microorganism such as Salmonella so that they can be used as a vaccine to raise an immune response in a subject. Preferably, the VLPs are delivered to mucosal sites, having the advantage of generating the immune response to the papillomavirus VLPs at the locations where infection actually takes place, as well as at other mucosal surfaces.

The term "papillomavirus" used herein covers both human and animal PVs. However, preferably, the papillomavirus is a human papillomavirus (HPV). About 70 different types of HPV have been cloned and characterized (denoted HPV1 to HPV70 . . . ), and all have an 8 kb double stranded genome which encodes different early products and two late products L1 and L2, and are either epitheliotropic or mucosatropic. L1 is a major capsid protein and is relatively well conserved among the different HPV types. For a review of the HPV types and their nucleic and amino acid sequences, see Human Papillomaviruses, "A Compilation and Analysis of Nucleic Acid and Amino Acid Sequences", 1994, ed. Myers et al, Theoretical and Biophysics Group T-10 Los Alamos National Laboratory. Clinically, the most important HPV types a are those that infect the anogenital tract, and that have high oncogenic risk and a high prevalence. This group includes HPV16, 18, 31, 45 and 56, with HPV16 alone accounting for more than 50% of invasive cancer in the anogenital tract, as well as being the most prevalent single type of HPV.

The papillomavirus proteins correspond to wild type major capsid proteins (e.g. L1 and/or L2) or may be chimeras of all or part of a HPV protein and a fusion partner. The fusion partner may be any immunogenic protein against which specific CTL would be targeted. This protein may be an HPV protein (e.g. E7, E6 or E2 of any HPV type), a protein from another pathogen or any tumour specific antigen. In one embodiment the HPV protein is L1 protein coexpressed with L2, with the fission partner expressed so that it is linked to the L2 protein.

It has been shown that chimeric VLPs can elicit anti-tumour immunity against carrier and inserted proteins in HPV16 tumour models. Thus, chimeric VLPs which induce E7-specific CTLs aimed to the killing of already HPV infected cells or HPV-associated premalignant lesions. In this event, induction of CTLs to eliminate already HPV infected cells appears therefore an appealing complement to the induction of neutralizing antibodies, and chimeric VLPs have been shown to induce both functions.

Thus, in one embodiment of the invention, Salmonella strains able to induce neutralizing antibodies and CTLs by expressing chimeric VLPs could be therapeutic at least for early or pre-malignant HPV lesions in which the downregulation of MHC I or other factors observed in more advanced cancers has not yet occurred Preferably, the prokaryotic microorganism is an attenuated strain of Salmonella. However, alternatively other prokaryotic microorganisms such as attenuated strains of *Escherichia coli*, Shigella, Yersinia, Lactobacillus, Mycobacteria, Listeria or Vibrio could be used. Examples of suitable strains of microorganisms include *Salmonella typhimurium, Salmonella typhi, Salmonella dublin, Salmonella enteretidis, Escherichia coli, Shigella flexeneri, Shigella sonnel, Vibrio cholera,* and *Mycobacterium bovis* (BC6).

Attenuated Salmonella strains are one of the best characterized mucosal vaccine carriers. Recombinant Salmonella stains that are attenuated yet invasive have been used as oral vaccine vectors to carry protective epitopes of several pathogens into the mucosal associated lymphoid tissue thus inducing mucosal, systemic and CTL immune responses against both the carrier and the foreign antigens (58,65,67, 69,75–77).

The currently licensed oral vaccine against typhoid fever *S. typhi* Ty21a (72) administered as a three-dose regimen of enteric-coated capsules ($10^9$ CFU/capsule) provided a 67% efficacy over a 3 year period. However, because the *S. typhi* Ty21a requires high and multiples doses in liquid formulation for higher efficacy, and its mutations are not yet all characterised (63,64,70,71,78), new attenuated Salmonella strains have recently been developed and tested in humans. These include nutritional auxotrophs in which pathways for biosynthesis of aromatic compounds have been interrupted ($\Delta$aro mutants). The $\Delta$aroA, $\Delta$purA mutants of *S. typhi* have been tested in human volunteers (32) and were shown to elicit specific cell-mediated immune responses but weak humoral responses. Other aro mutants (aroC and aroD) were insufficiently attenuated and caused fever and bacteremia (79). A double mutant $\Delta$aroC $\Delta$aroD Ty2 (CVD 908) was safe and elicited IgG antibodies against LPS in 80% of the immunized adult volunteers (73, 80). *S. typhi* mutants were also generated in which the adenylate cyclase (cya) and the cAMP receptor (crp) genes were deleted. These gene products are required for the transcription of many genes and operons that control transport processes, expression of fimbriae, flagella and some outer membrane proteins. One mutant $\chi$3927 ($\Delta$cya $\Delta$crp Ty2) was tested and shown to be immunogenic but some volunteers developed fever and vaccine bacteremia (79). Therefore, a novel strain, $\chi$4073, was constructed by deleting a third gene (cdt) responsible for colonization of deep tissue (66,68,74). This strain was administered to volunteers and proved to be completely safe at doses up to $5 \times 10^8$ CFU and generated a seroconversion in 80% of the volunteers (66).

Preferred attenuated Salmonella strains include mutants in a two-component regulatory system, the PhoP/PhoQ genes. These genes affect expression of a number of other genes and are responsive to phosphate levels and to environmental conditions expected to be experienced by Salmonella residing within macrophages. Preferred example of these mutants are the PhoP$^c$ strains used in the examples described below. Recently, a PhoP/PhoQ-deleted *Salmonella typhi* (ty800) has been shown to be safe and immunogenic in humans (81).

A still more preferred example of such a mutant is one in which a β-aspartate semialdehyde dehydrogenase (asd) vector is incorporated in order to maintain selective pressure in vivo to maintain the expression of HPV16 VLPs. This is surprising as it has previously been reported that such mutant, when administered nasally at least, induces much lower levels of anti-HPV16 L1 VLPs than intact PhoP$^c$ strains (see Benyacoub et al, 16$^{th}$ International Papilloma Conference, Siena, Sep. 5–12, 1997), surviving to a lesser extent and with absence of L1 expression.

More preferred is use of a PhoP$^c$ $\Delta$asd strain that places $\Delta$asd and the HPV VLP protein or its fusion together in a plasmid that has a 'medium copy' number eg. 15 to 20, rather than a higher copy number. Eg. having a pBR ori such as plasmid pYA3342.

As mentioned above, the attenuated strain of the prokaryotic microorganism is transformed with a nucleic acid encoding one or more major papillomavirus capsid proteins. The inventors found for the first time that, when this nucleic acid is expressed in the microorganisms, the capsid proteins produced assemble correctly to form VLPs, making them especially suitable for the vaccination of subjects against papillomaviruses. Preferably, the major viral capsid protein is L1, optionally additionally including nucleic acid encoding L2 protein. As discussed above, the capsid protein may be linked to a fusion partner such as another antigen.

In a further aspect, the present invention provides a composition comprising one or more of above attenuated prokaryotic microorganisms, optionally in combination with a physiologically acceptable carrier. Preferably, the composition is a vaccine, especially a vaccine for mucosal immunization, e.g. for administration via the oral, rectal, nasal, vaginal or genital routes. Our earlier studies using recombinant Salmonella expressing hepatitis B virus antigen (18) showed that vaccination via any of these routes produces a sIgA response in the mucosal secretions at other sites. Advantageously, for prophylactic vaccination, the compositions comprises one or more strains of Salmonella expressing a plurality of different VLPs, e.g. VLPs from different papillomavirus types. This has the advantage of improving the protective effect of the vaccine to a range of challenges by the different papillomavirus types. For therapeutic vaccination, subsequent chimeric VLP constructs can comprise fusion products of various HPV type L1 capsids with the same L2 fusion partner.

In a further aspect, the present invention provides an attenuated strain of a prokaryotic microorganism described above for use as a medicament, especially as a vaccine.

In a further aspect the present invention provides the use of an attenuated strain of a prokaryotic microorganism transformed with nucleic acid encoding papillomavirus virus major capsid protein, wherein the protein assembles in the microorganism to form virus like particles, in the preparation of a medicament for the prophylactic or therapeutic treatment of papillomavirus infection or anogenital cancer, especially cervical cancer.

Generally, the microorganisms or VLPs according to the present invention are provided in an isolated and/or purified form, i.e. substantially pure. This may include being in a composition where it represents at least about 90% active ingredient, more preferably at least about 95%, more preferably at least about 98%. Such a composition may, however, include inert carrier materials or other pharmaceutically and physiologically acceptable excipients. A composition according to the present invention may include in addition to the microorganisms or VLPs as disclosed, one or more other active ingredients for therapeutic use, such as an anti-tumour agent.

The compositions of the present invention are preferably given to an individual in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated Prescription of treatment, eg. decisions on dosage etc, is within the responsibility of general practioners and other medical doctors.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration.

Examples of techniques and protocols mentioned above can be found in Remigton's Pharmaceutical Sciences, 16th edition, Osol, A. (ed), 1980.

In a further aspect, the present invention provides a method for producing assembled papillomavirus virus like particles comprising culturing an attenuated strain of a prokaryotic microorganism transformed with nucleic acid encoding papillomavirus virus major capsid protein wherein the protein is expressed and assembles in the microorganism to form virus like particles. Preferably, the method additionally comprises the step of recovering the VLPs from the prokaryotic microorganism.

In a further aspect, the present invention provides the use of a papillomavirus VLP as obtainable by transforming an attenuated prokaryotic microorganism with nucleic acid encoding the VLPs and expressing the nucleic acid to produce assembled VLPs, in a diagnostic method. in one embodiment, present invention provides a method for detecting the presence of anti-papillomavirus antibodies in a sample from a subject comprising immobilizing the HPV VLPs on a solid support, exposing the support to the sample and detecting the presence of the antibodies, e.g. using ELISA.

Preferred embodiments of the present invention will now be described by way of example and not limitation with reference to the accompanying drawings.

BRIEF DESCRIPTION OF THE FIGURES

FIG. 1. HPV16 L1 expression in the PhoP$^c$/HPV strain. Salmonella were grown overnight and prepared as indicated in Material and Methods. A. Commassie blue staining of a 10%SDS PAGE gel; Lane M : Molecular weight marker; Lane 1: total lysate of the PhoP$^c$ strain Lane 2: total lysate of the PhoP$^c$/HPV strain, a unique 57kDa protein is indicated with an arrow. B. Immunoblot using anti-HPV16-L1 mAb of the total and fractionatd PhoP$^c$/HPV lysate. Lane tot: total lysate, Lane 1 to 25: different fractions obtained after fractionation of the PhoP$^c$/HPV lysate through a 10–40% sucrose gradient, the heavier fraction of the gradient being in lane 1. The 57kDa protein band identified as being L1 is indicated (arrow).

FIG. 2. HPV16 L1 assemble into VLPs. Electron micrographs of (A) PhoP$^c$/HPV16 VLPs and (B) Baculo-derived HPV16 VLPs. In A, fractions 7 to 13 of PhoP$^c$/HPV lysate (FIG. 1) were pooled. The samples were negatively stained with phosphotungstic acid. Bar represents 53 nm.

FIG. 3. Anti-HPV16VLP and anti-LPS systemic and mucosal antibody responses after nasal immunization with the PhoP$^c$/HPV strain. Three 6-week-old BALB/c female mice were immunized with $5 \times 10^7$ CFU, sampled at the indicated weeks, sacrificed and bled at week 27. Data are expressed as the geometric means of the reciprocal dilutions of specific IgG in serum and specific IgA per microgram of total IgA or IgG per microgram of total IgG in secretions. Error bars indicate the standard errors of the means.

FIG. 4. HPV viral cycle and vaccination strategies. In the left portion of the figure the HPV productive viral cycle during keratinocyte differentiation is schematically drawn (early infection-CIN I). A late stage of infection (CIN III-tumour) in which the HPV DNA is integrated into the host genome is shown on the right. Different protective immune mechanisms are shown with arrows indicating the sites of action. Antibody-dependent cellular cytotoxicity (ADCC) mechanims which require viral antigens to be expressed at the surface of cells are not indicated.

FIG. 5. In vitro neutralization of HPV16 pseudotype virus infection of mouse C127 cells (A) no virus added. (B-H) Equal aliquots of an HPV16(HPV1) pseudotype virus containing extract was added The aliquots were preincubated with (B) no antibodies, (C) BPV1 neutralizing MoAb B1.A1, (D) HPV16(BPV1) neutralizing MoAb H16.E70, (E) mouse preimmune sera, (F) mouse#4 immune sera$_{(week\ 27)}$, (G) mouse#5 immune sera$_{(week}$ 27), (H) mouse#4 immunes sera$_{(week\ 27)}$.

Nasal immunisations were performed three times weekly with either 20 μl PBS (A) or 5 μg of purified HPV16 VLPs+5 μg of cholera toxin (CT)(E) and two times at week0 and week2 with 10 CFU of PhoP$^c$/HPV16 L1 (b), $\chi$4550/pYA34L1 (C) and $\chi$4550/pYA32L1 (D). All mice were challenged with 5 10$^5$ C3 cells into the flank two weeks after the last immunisation. The mean volume of the tumours in each group are shown, while the number of mice harbouring a tumour/number of mice injected is indicated at Day 17.

FIG. 7 shows coexpression of L1 and L2 in PhoP$^c$/HPV16 L1-L2. Blot A was revealed with an anti-L2 antibody, while blot B was revealed with anti-L1 antibody (Camvir).

FIG. 8 shows the expression of L1 in *E. coli* BL12 pET 3D-L1. Identical amounts of bacteria were loaded (3×10$^6$ CFU) after 3 hours incubation with IPTG and the blot was revealed with an anti-L1 antibody.

DETAILED DESCRIPTION

Materials and Methods

Plasmid Construction and Bacterial Strains Used

Plasmid pFS14nsd HPV16-L1 was constructed by exchanging in the plasmid pFS14 NSD (54) the hepatitis B nucleocapsid gene (HBcAg, NcoI-HindIII fragment) for a NcoI-HindIII fragment encoding the HPV16-L1 open reading frame. The HPV16-L1 NcoI-HindIII fragment was generated by Polymerase Chain Reaction (PCR) using the baculovirus expression plasmid pSymwtVIHPV16 114/B-L1+L2 (23) as a template with a 28 mer containing a NcoI site 5'-GGGCCATGGCTCTTTGGCTGCCTTAGTGA-3' (SEQ ID NO:1) and a 27 mer containing a HindIII site 5'-GGGAAGCTCAATACTTAAGCTTACG-3'(SEQ ID NO:2). The final construct containing the Tac promoter places the HPV16-L1 ATG at position +8 relative to the Shine-Dalgamo sequence and introduces a change in the second amino acid which becomes an alanine instead of the serine encoded by the original sequence. Sequencing of the entire L1 open reading frame was carried out (MycrosynthAG) and no further nucleotide change was observed Plasmid pFS14nsd HPV16-L1 was amplified in *E. coli* JM105 and then electroporated as described previously (50) into bacterial strain CS022. This strain is derived from the ATCC 14028 strain, into which the pho-24 mutation was introduced by P22 transduction, resulting in attenuation in both virulence and survival within macrophages in vitro (PhoP$^c$, (35)). The resultant recombinant strain is called PhoP$^c$/HPV hereafter.

Expression of HPV16-L1 in Salmonella and VLPs Purification

After overnight growth at 37° C. the recombinant bacteria were lysed by boiling in Laemmli buffer containing 5% SDS. The lysates were separated on 10% SDS/PAGE gels and expression of L1 was analyzed by Western blot using HPV16-L1 mAb CAMVIR-1 (33) as prey antibody, an alkaline-phosphatase conjugated goat anti-mouse IgG (Sigma) as secondary antibody and BCIP/NBT (Boehringer) as substrate.

To prepare VLPs, bacteria were lysed by sonication and the lysate fractionnated on a 10%–40% sucrose gradient in Phosphate Buffer Saline (PBS) containing 1M NaCl for 1 hour at 40 Krpm using a TST41.14 rotor. Fractions of the gradient were then analysed for the presence of the L1 protein by Western blot. The fractions of high sedimentation containing the L1 protein were pooled, dialyzed against PBS/0.5M NaCl. VLPs were pelleted for 1 h at 50Krpm using a TST65.1 rotor, adsorbed to carbon-coated grids, negatively stained with phosphotungstic acid and examined with a Philips electron microscope.

Purification of HPV16 VLPs Expressed in Insect Cells from a Recombinant Baculovirus The transfer vector pSynwtVI.HPV16 114B-L1+L2 (23) was cotransfected with the linearized genome of baculovirus Baculo-Gold, Pharmingen) using the calcium-phosphate method into SF9 cells. The recombinant baculoviruses were plaque-purified and propagated by standard methods (39). Baculo-derived HPV16 VLPs were purified as described previously (23).

Immunization and Sampling of Mice

Six-week-old female BALB/c mice were immunized at day 0 and at week 14 by hew nasal route with 5×10$^7$ CFU of inoculum. Blood, saliva and genital samples were taken as described previously (18). All samples were stored at –70° C.

ELISA

The amount of total IgA, anti-LPS IgA and IgG antibodies in samples were determined by enzyme-linked immunosorbent assay (ELISA) as described previously (18). For the anti-HPV16 VLP, ELISA plates were coated with 10 ng of a preparation of baculo-derived HPV16 VLPs in PBS (total protein content was determined with a BioRad Protein assay with BSA as standard). This amount of VLP was saturating in our ELISA test. Endpoint dilutions of samples were carried out. The specific IgA or IgG amounts are expressed as reciprocal of the highest dilution that yielded an OD$_{492}$ four times that of preimmune samples. These reciprocal dilutions were normalized to the amount of total IgA or IgG in saliva and genital washes. ELISA plates were also coated with 10 ng of baculo-derived HPV16 VLPs in 0.2M carbonate buffer pH9.5 to determine the titer of antibodies recognizing unfolded VLPs (14).

In vitro HPV16 Neutralization Assay

Infectious pseudovirions consisting of HPV capsid made of L1 and L2 surrounding the bovine papillomavirus type 1 (BPV 1) genome, designated HPV16(BPV1), were generated as recently described (43). Briefly, BPHE-1 hamster cells harbouring autonomously replicating BPV1 genomes were co-infected with defective recombinant Semliki forest viruses that expressed L1 and L2 virion capsid genes of HPV16. Infectious pseudotype HPV16 virus in cell extracts was quantitated by the induction of transformed foci in monolayers of mouse C127 cells. Neutralizing activity was measured after preincubation of the cell extracts with mouse sera diluted 1:50 (1.0 ml final volume) in culture medium. Mouse monoclonal antibodies H16.E70 and B1A1 were generated against recombinant baculovirus expressed HPV16L1 VLPs and BPV16 VLPs respectively, and used at a 1:100 dilution. H16.E70 and B1.A1 served as positive and negative controls for HPV16 (BPV 1) neutralization, respectively.

Results

HPV16-L1 is Expressed in PhoP$^c$ and VLP Assemble

Figure 1A:
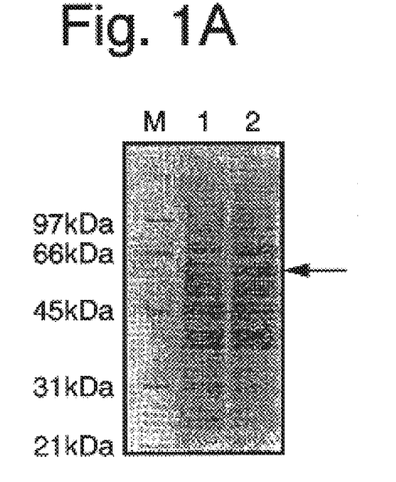

The open reading frame of the major protein L1 of HPV16 was cloned in the plasmid pFS14 NSD (53). L1 is constitutively expressed under the control of the Tac promoter in *S. typhimurium*. A unique 57kDa protein detected in the lysate of PhoP$^c$/HPV overnight cultures (FIG. 1A), was identified as HPV16 L1 by Western immunoblot using an anti-HPV16-L1 monoclonal antibody (CAMVIR, (33), FIG.

Figure 1B:
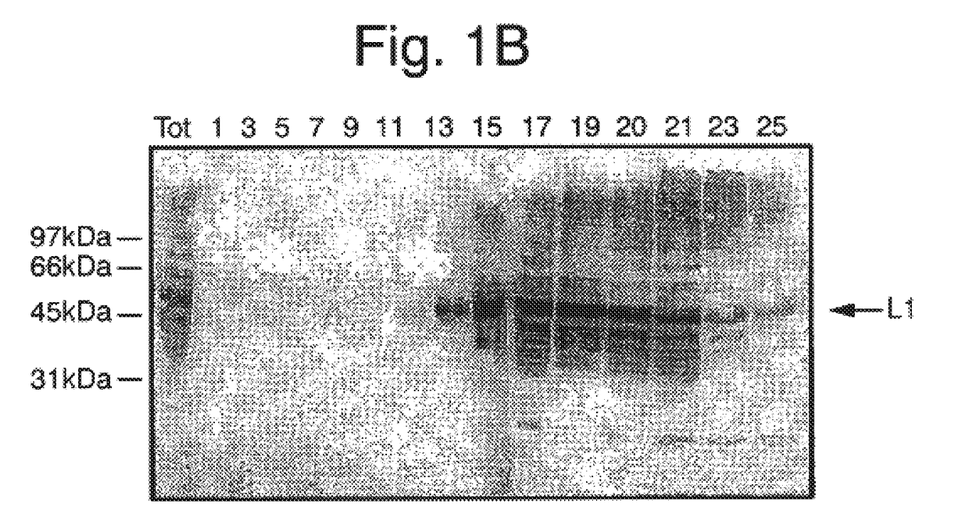
Figure 2A:
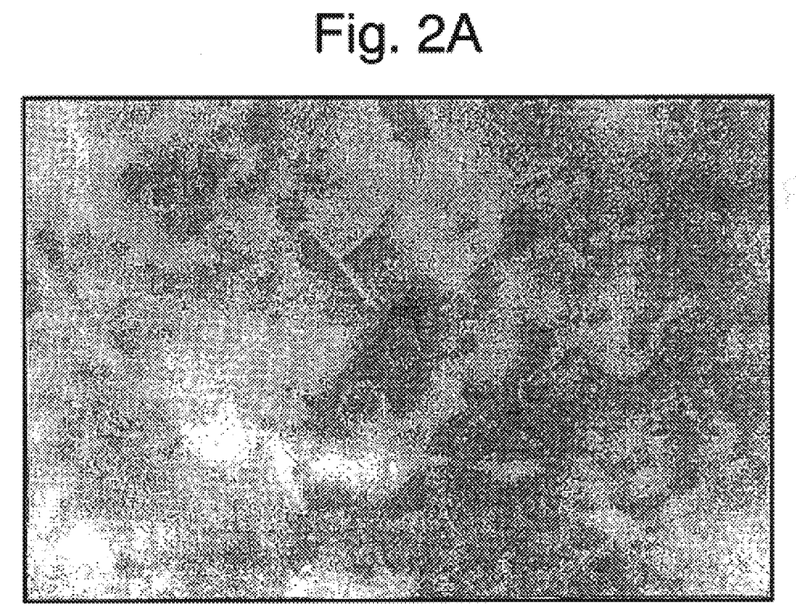
Figure 2B:
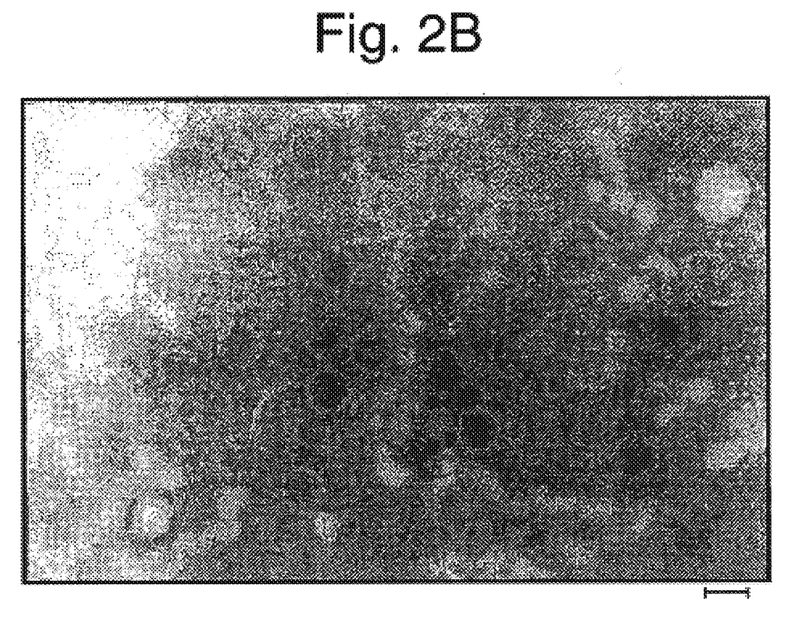

1B). To determine whether he L1 protein expressed by PhoP$^c$/HPV assembled into VLP, the bacterial lysate was fractionated trough a 10–40% sucrose gradient and the heavier fractions containing the L1 protein (FIG. 1B) were analyzed by electron microscopy. Spherical particles typical of PV capsids were recovered from the bacterial preparation (FIG. 2A) but the bacterial VLPs appeared more polymorphic in size with diameters ranging from 40 to 55 nm (FIG. 2A) when compared to ~55 nm VLPs expressed in insect cells (FIG. 2B).

Figure 3:
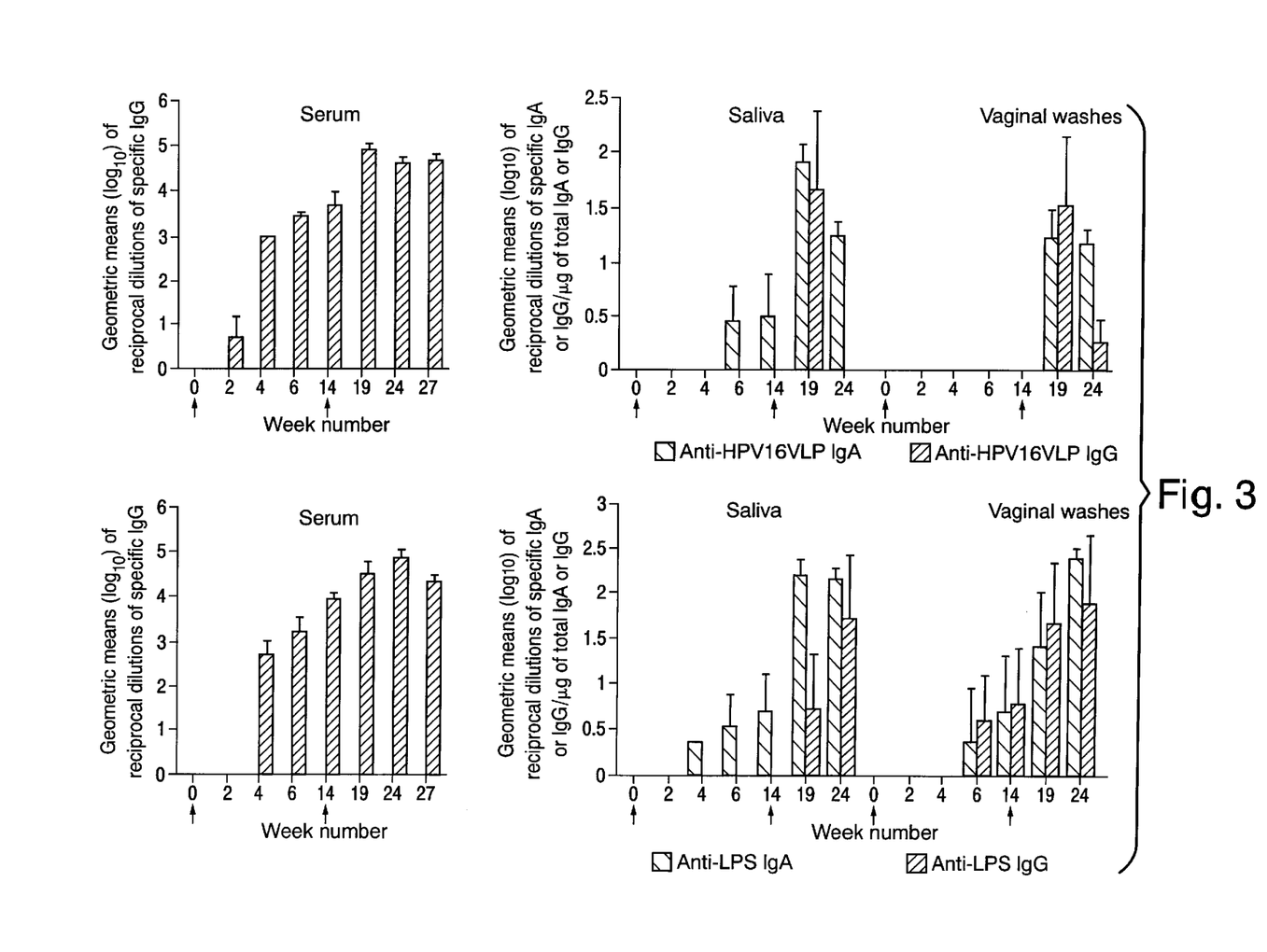

Nasal Immunization with the PhoP$^c$/HPV Strain Induces Systemic and Mucosal Antibody Responses Since nasal immunization using recombinant Salmonella was shown to elicit strong vagina sIgA responses against an expressed foreign antigen (18), we immunized mice nasally with the PhoP$^c$/HPV strain ($5 \times 10^7$ CFU). Samples of blood, saliva and vaginal washes were taken 0, 2, 4, and 6 weeks after immunization. The immune responses against both the carrier, i.e. anti-LPS and the carried antigen, i.e. anti-HPV16 VLP, were determined. Serum HPV16 VLP specific IgG (FIG. 3) were detected after 2 weeks in one mouse and after 4 weeks in all mice. The response peaked after 6 weeks at relatively low titers and persisted at least until week 14. At that time, no HPV16 VLP specific antibodies were detected in vaginal secretions, while one mouse had low titers of IgA in the saliva. The systemic and the mucosal immune responses against LPS were relatively low (FIG. 3), but similar to those elicited by the PhoP$^c$/HBc strain (18) suggesting a normal take of PhoP$^c$/HPV Salmonella by the mice. The low anti-LPS response observed after nasal immunization incited us to perform a booster immunization. Thus, a second nasal immunization was performed at week 14 and samples were taken 5 and 10 weeks later (week 19 and 24 respectively). The second immunization induced, 5 weeks later (week 19), a 15 fold increase of anti-HPV16 VLP IgG in serum, as well as anti-HPV16 VLP IgA in the vaginal washes (FIG. 3) from the three mice. Anti-HPV16 VLP IgG were also found in vaginal washes but only in two mice at week 19 and titers were again almost undetectable at week 24 (FIG. 3). Anti-HPV16 VLP IgA and IgG were also found in the saliva of the three mice in amounts comparable or slightly higher to those found in vaginal washes.

Anti-HPV16 VLP Antibodies Recognize Only Folded VLP

In order to examine whether the immune responses induced by the PhoP$^c$/HPV strain generated conformational antibodies directed against native but not unfolded VLPs, we measured by ELISA (Table 1) the binding of antibodies, in the samples from the immunized mice, to baculo-derived VLPs in PBS (native form) or in carbonate buffer (pH 9.5, unfolded VLP, (14)). The specific IgG or IgA elicited by the PhoP$^c$/HPV strain very poorly recognizes unfolded VLPs suggesting that the majority of L1 were folded into highly ordered structures when expressed in PhoP$^c$/HPV (Table 1).

In vitro Neutralizing Activity of the Immune Sera

In previous studies of baculo-derived VLPs, neutralizing activity and protection from experimental infection generally correlated with ELISA reactivity to native VLPs. We therefore wished to determine if the conformationally dependent anti-VLP antibodies elicited by the live Salmonella vaccine were also neutralizing. Although no infectivity assay or source of the virus currently exists for authentic HPV16, it has recently been demonstrated that HPV16 capsid proteins can encapsidate autonomously replicating BPV1 genomes resulting in HPV16(BPV1) pseudotype virions whose infectivity can be monitored by focal transformation of cultured mouse fibroblasts (43). We therefore used the HPV16(BPV1) infectivity assay to examine the neutralizing activity of the mouse sera generated above. Each of the three immune sera displayed strong neutralizing activity against HPV16(BPV 1) (FIG. 5), but did not neutralize BPV1 virions (data not shovel). The preimmune sera had no neutralizing activity. The neutralizing activities of the immune sera appeared to correlate with the titers in the native VLP ELISA, although the sera were only tested at a single dilution.

Tumour Protection Assay in the HPV16 Mouse Tumour Model

Figure 6:
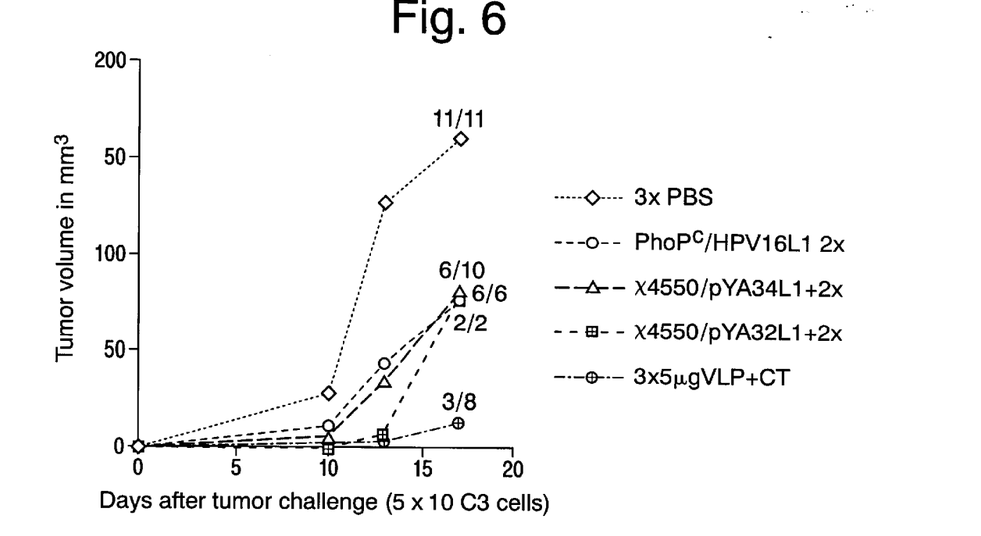
FIG. 6 shows the results of tumour growth experiments in mice immunized with Salmonella HPV producing strains.
Figure 7A:
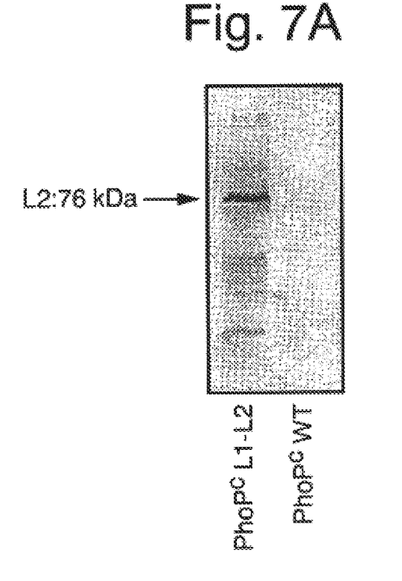
Figure 7B:
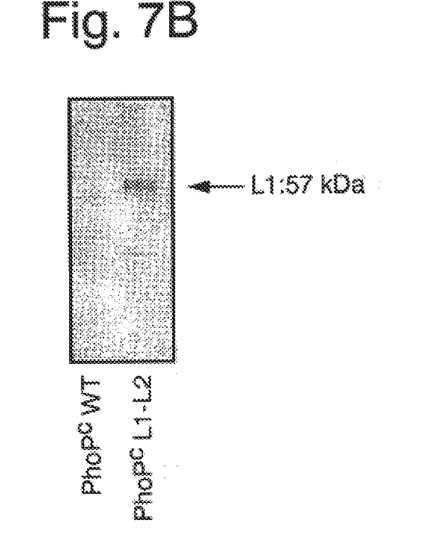

It has been recently shown that the growth syngeneic tumour cells (C3) injected into the flank of C57BL/6 mice was inhibited by a subcutaneous immunization with purified HPV16 cell (84). We have tested whether nasal immunization with purified VLPs and recombinant Salmonella/HPV strains was able to induce the same effect. Specifically, we have tested the following stains: PhoP$^c$/HPV16 L1 (86) and the $_\chi$4550 (56) expressing either high levels ($_\chi$4550/pY34L1) or low levels ($_\chi$4505/pYA32L1) HPV16 L1. Tumour growth in the different groups of mice is shown in FIG. 6. Our preliminary results demonstrate that nasal immunization with purified VLPs is effective and that all the Salmonella/HPV strain tested induced partial tumour protection. Of interest, is the strain $_\chi$4550/pYA34L1 that prevented complete tumour growth in 4/10 mice.

Coexpression of the L2 Protein into PhoP$^c$/HPV16

The L2 OR17 was cloned downstream of the L1 ORF by PCR into the plasmid pPSnsdHPV16 L1 (86). The PCR reaction included a 5' specific oligonucleotide that contained a synthetic Shine-Dalgarno sequence in order to allow translation of 12 from a polycistronic L1–L2 RNA. The resultant PhoPC/HPV16 L1+L2 recombinant strain expressed both L1 and L2 and VLPs assembled in amount similar to the parent PhoPC/HPV16 L1 strain as assessed by a sandwich ELISA. This suggests that by fusing the E7 ORF to the L2 ORF, in the PhoP$^c$/HPV16 L1+L2 strain, a chimeric VLPs would also assemble and such recombinant Salmonella strain used to induce HPV16 E7-CTLs.

High Level Expression of L1 in the Inducible E. coli PET Expression System

Figure 8:
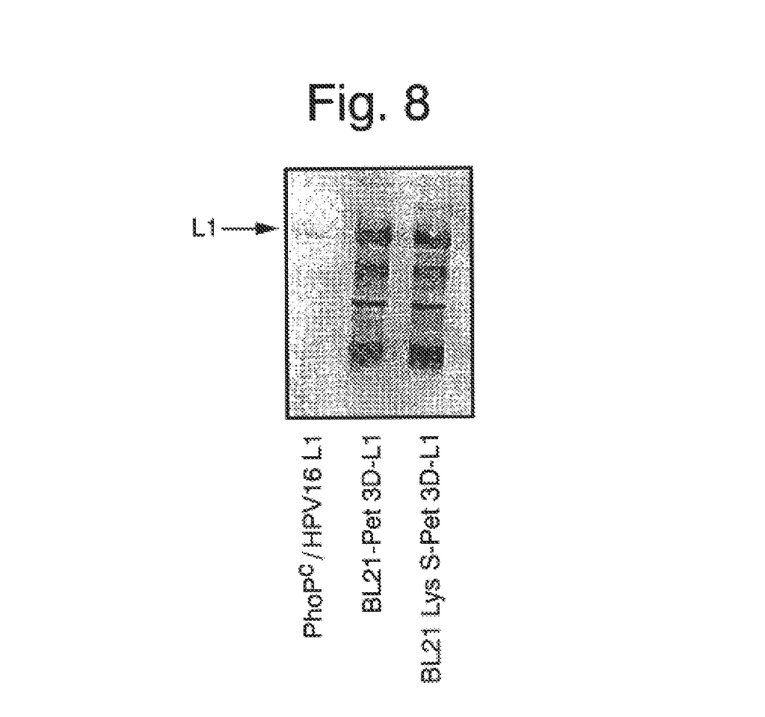

The L1 ORF was cloned in the plasmid pET3 (Novagen). L1-expression driven by a T7 promoter was assessed in the strain BL21apLysS (expressing T7 polymerase upon IPTG induction). After IPTG induction, a 10 fold higher level of L1 expression/bacteria was achieved in comparison to the Salmonella PhoP$^c$ strain (see FIG. 8). The lysate of this recombinant E. coli formed a band at a density of VLPs in a CsCl density gradient, suggesting that the VLPs self-assembled in this bacteria.

Induction of Therapeutic Immune Response with Δasd Mutants

A deletion in the aspartate-β-semialdehyde dehydrogenase (asd) gene was introduced into the PboP$^c$ strain described above by P22Htint bacteriophage transduction. The original P22Htint lysate propagated on the $_\chi$3520 S. typhimurium ΔasdAl zhf-4::Tn10 provided by Dr R Curtiss III). A tetracycline sensitive PhoP$^c$ Δasd strain was then selected (see Maloy et al (1981) J. Bacteriol p1110–1112 incorporated herein by reference). A NcoI-HindIII fragment containing HPV16 L1 (from the plasmid pYS14nsd HPV16-L1-see Nardellihaefliger et al (1997) Infection & immunity 65 (8) 3328–3336 incorporated herein by reference) was cloned into the NcoI-Hind-III sites of the plasmid pYA3342–(provided by Dr R Curtiss III) and the resultant recombinant PhoP$^c$ Δasd/HPV16 L1 strain was used in a tumour protection assay as follows.

Nasal immunisations were performed at week 0 and week 2 with 10 μl of PBS(A in FIG. 9), with 1×10⁷ CFU of recombinant PhoP$^c$ Δasd (B in FIG. 9) or 1×10⁷ CFU recombinant PhoP$^c$ Δasd/HPV16 L1. All mice were challenged with 5×10⁵ C3 cells into the flank four weeks after the last immunisation.

Figure 9:
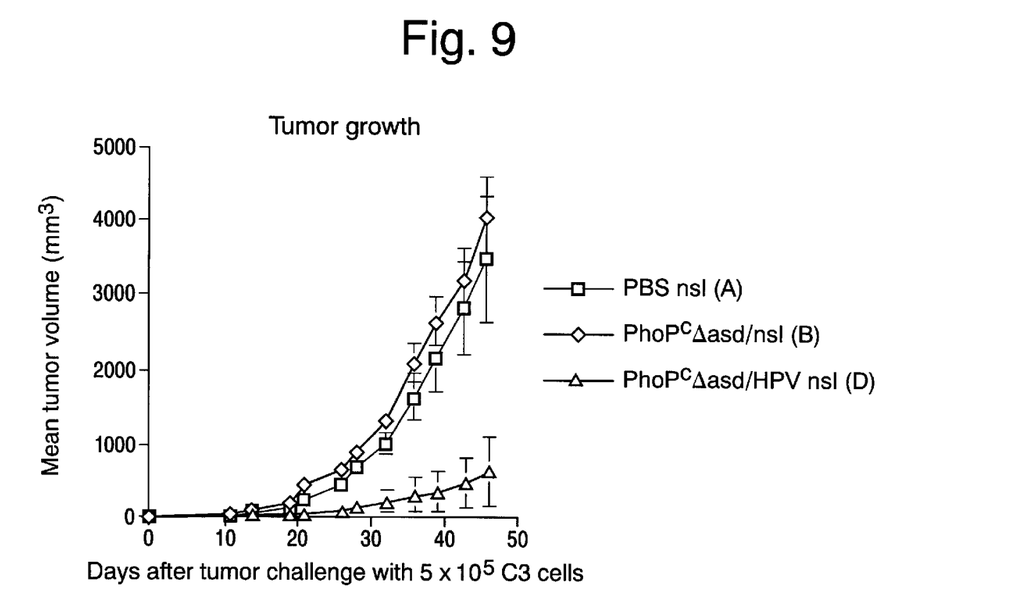
FIG. 9 shows the results of tumour growth experiments with PhoP$^c$ Δasd mutants having or lacking the ability to express L1 VLPs. Plots are for PBS (A), PhoP$^c$ Δasd/nasal (B) and PhoP$^c$ HPVL1 nasal (C).
Figure 10:
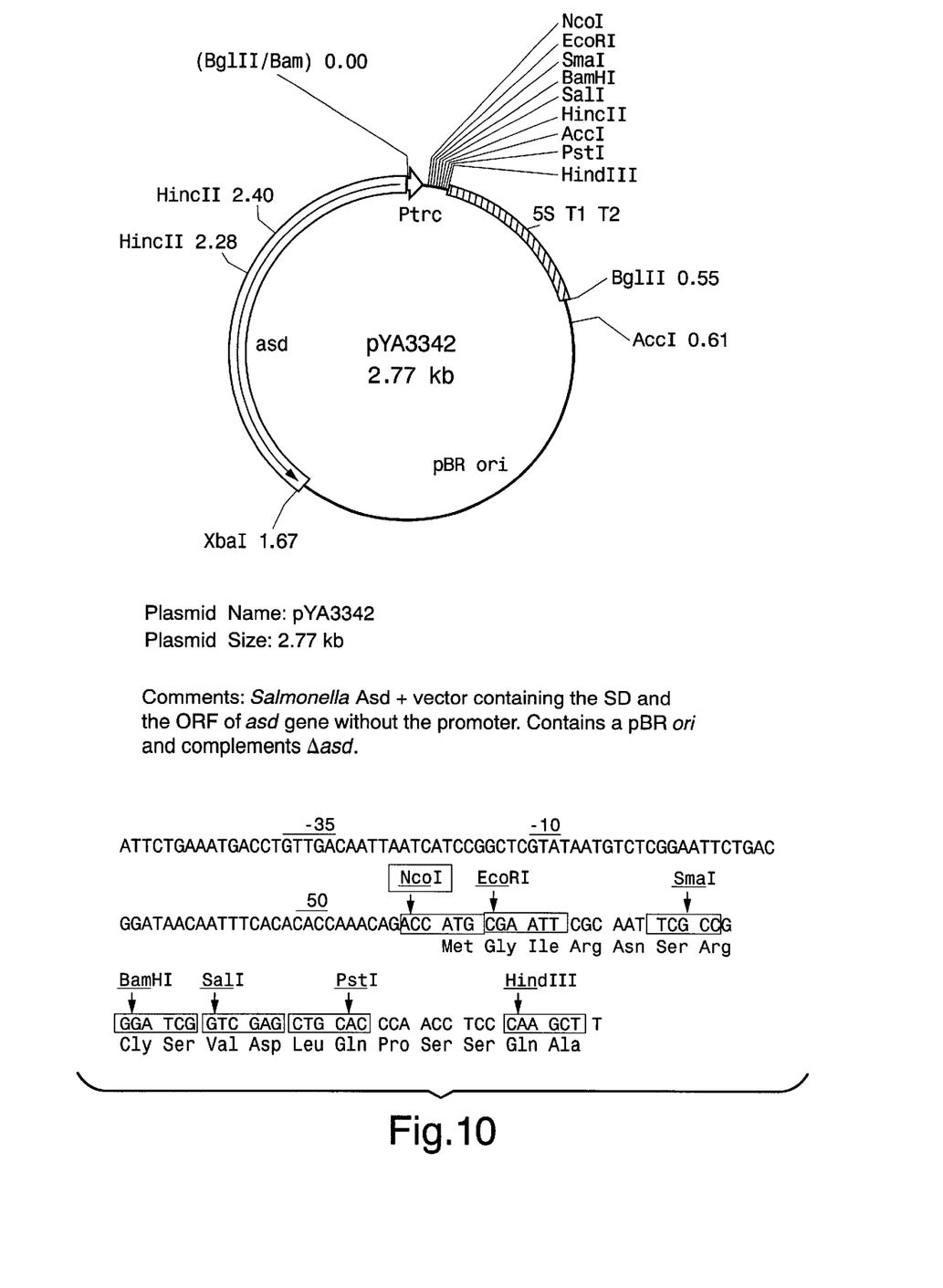
FIG. 10 is a map showing the essential characteristics of plasmid pYA3342.

Results, displayed graphically in FIG. 9, show the protection against tumour growth conferred by the immunisation with the PhoP$^c$ Δasd/HPV16 L1, No protection was conferred by the parent strain that lacks expression of the L1 antigen PhoP$^c$ Δasd.

Discussion

In this study, we demonstrate that an attenuated Salmonella strain expressing the major capsid protein of HPV16 is a promising vaccine candidate against HPV16 infection, as the VLPs that are assembled by this recombinant bacteria can induce serum as well as genital VLP-specific conformational antibodies. The results above also show that the antibodies are able to neutralize HPV16 viruses. These results could be readily extrapolated by the skilled person to other types of HPV or other papillomaviruses, or other prokaryotic microorganisms.

The life cycle of papillomavirus is intimately associated with the differentiation of the epithelial cells in skin or the oral and genital mucosa (5,19,40,62). It is believed that viruses gain access to the basal epithelial cells through mucosal abrasions (21). Upon infection of the cervical epithelium for instance, the viral DNA released in the cytoplasm of the basal cells migrates into the nucleus where it remains episomic and early genes are transcribed leading to a low rate of cell proliferation and the thickening of the basal layer (Cervical intraepithelial neoplasia type I, CIN I). As the infected epithelial cells migrate through the suprabasal layer and undergo differentiation, the episomal viral genome replicates reaching ~1000 copies per cell (29). Concomitant to viral DNA amplification, late genes become expressed and capsids assemble in terminally differentiated keratinocytes (FIG. 4), thus facilitating a new round of infection. In high grade lesions (CIN III and carcinoma) the entire epithelium consists of undifferentiated basal cells in which the viral DNA has been integrated into cellular DNA. In these cells, the E6/E7 gene products constitute the major HPV proteins expressed and viruses are no longer produced.

Figure 4:
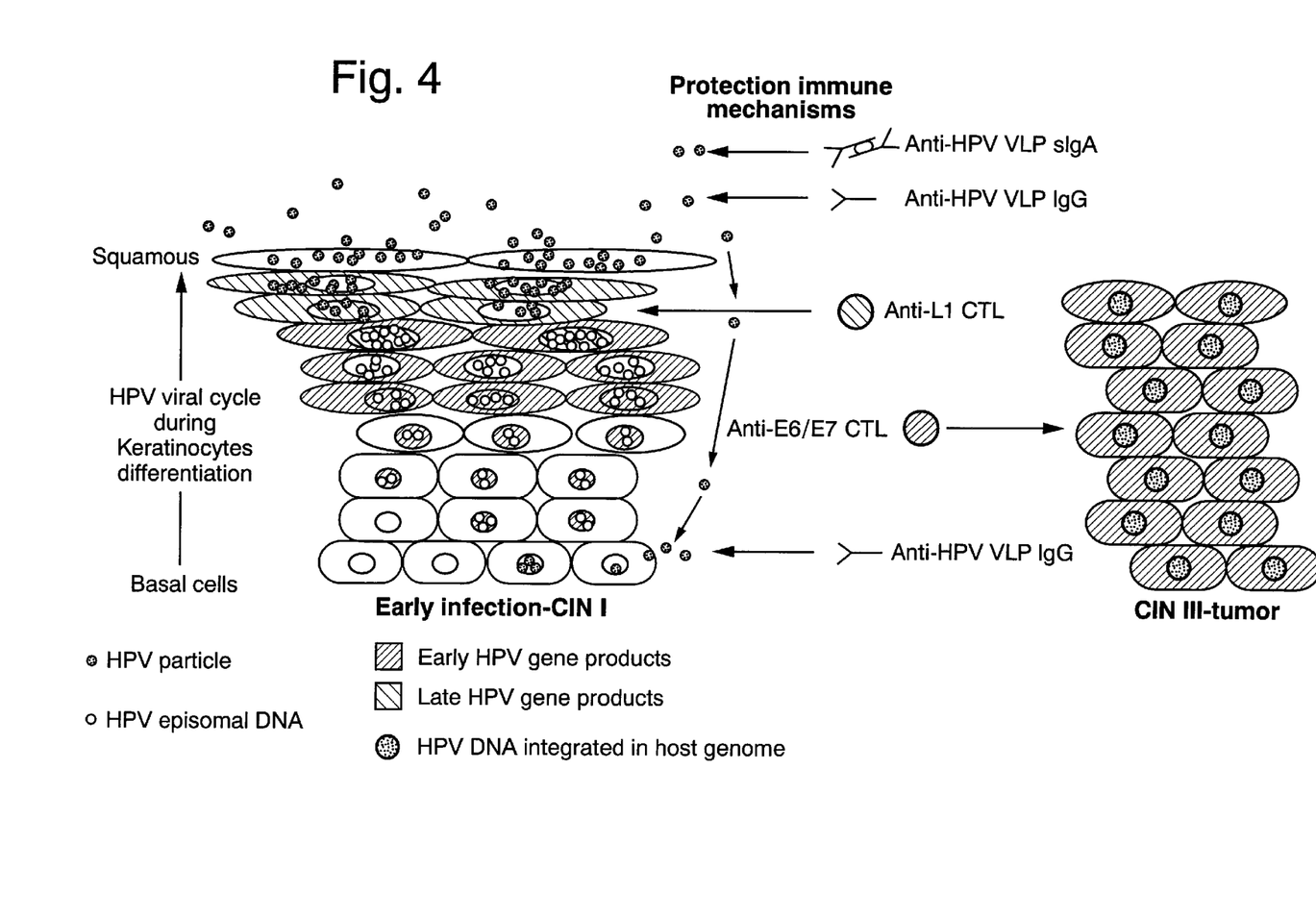
Figure 5A:
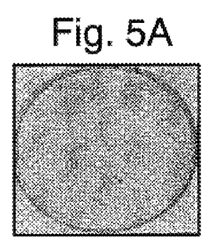
Figure 5B:
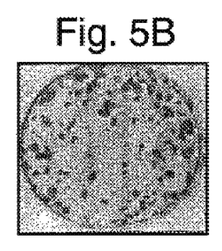
Figure 5C:
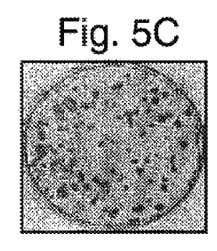
Figure 5D:
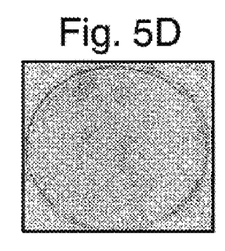
Figure 5E:
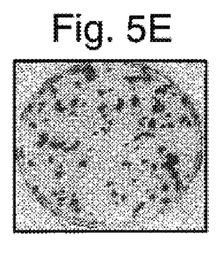
Figure 5F:
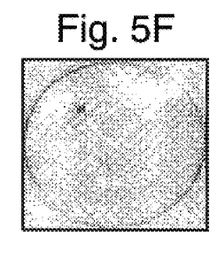
Figure 5G:
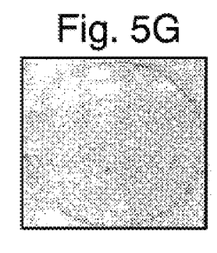
Figure 5H:
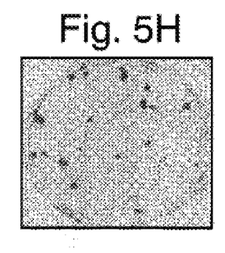

Based on our knowledge of HPV pathogenesis, it appears that two arms of immunity (humoral and cellular) have to be effective to prevent viral infection, to decrease the local viral load, or to cure tumors (FIG. 4, see also (59)). A local or systemic humoral immune response with neutralizing antibodies is likely to block early infection, while a cellular response may contribute to the elimination of untransformed or transformed infected cells. An ideal vaccine should trigger the two types of response, although the immunological correlate of protection and of cure have not been identified so far.

Prophylactic vaccines inducing type-specific neutralizing conformational (anti-VLP) antibodies have been shown to prevent CRPV or COPV infections in cottontail rabbit (4) or dog (57), respectively. In both cases serum neutralizing antibodies where generated by vaccination with self-assembled PV capsids. By analogy, neutralizing antibodies to HPV16 capsid in cervical secretions are expected to prevent infection. Since the precise mucosal site where early HPV infection takes place is not known, it is difficult to predict whether sIgA antibodies acting from the lumenal site or circulating IgG antibodies reaching the basal layers will be most efficient.

The elimination of HPV-infected cells or tumor cells requires a cellular immune response with cytotoxic T lymphocytes (CTL) recognizing viral antigens presented by MHC class I molecules on the infected cells. Therapeutic vaccines aimed at eliminating HPV-induced tumors have been generated using either peptides corresponding to T cell epitopes from the E6/E7 oncogenes or E6/E7 expressing vaccinia viruses. Both were shown to elicit CTLs and in some cases tumor regression was observed (3,6,7,12,13,34). One of the major problems, however, is that MHC class I molecules are down-regulated in the differentiated keratinocytes that produce viruses or in tumour cells (9).

Since both humoral and cellular immunity are believed to control HPV infection and since local and systemic responses are desirable, an efficient vaccine should reach inductive sites associated with mucosal surface and/or peripheral lymph nodes. Live bacterial vaccines are known to cross mucosal surfaces and elicit humoral or cellular responses (41). Recombinant and attenuated enteropathogenic bacteria, such as Salmonella, represent ideal antigen delivery systems, because they efficiently cross all mucosal surfaces to gain access to both mucosal organized lymphoid tissue (MALT) or draining lymph nodes. They exploit the two basic sampling systems mediating uptake of mucosally administered antigens including M cells in simple epithelia and dendritic cells both in simple and stratified epithelia (38). We have selected a *Salmonella typhimurium* strain attenuated for macrophage survival, because long lasting antibody responses were elicited by a single nasal, oral, rectal or vaginal administration of recombinant bacteria expressing a foreign antigen (18). In that study, the best genital responses were obtained after nasal immunization. In the airways, antigen uptake occurs through M cells found in NALT, the nasal associated lymphoid tissue (25) and BALT, the bronchial associated lymphoid tissue (55). The primed IgA-expressing lymphocytes then migrate into cervical and uterine tissues where they produce polymeric IgA antibodies, which are transported across the epithelium by the polymeric Ig receptor (26–28). Intraepithelial dendritic cells in the bronchial epithelium also play a major role in antigen presentation by taking up the antigens in the respiratory epithelium and carrying them to distant draining lymph nodes where priming occurs (17). This probably explains why nasal immunization is so efficient in triggering both local and systemic antibody responses.

Antigens expressed in Salmonella strains can also elicit cellular responses with specific CTLs (1,16,58). Depending on which viral antigen is expressed, specific CTLs recognizing infected cells at different stages of differentiation could be generated (FIG. 4). For instance, E7-specific CTLs were generated by immunizing mice with recombinant Salmonella expressing HPV16 E7 epitopes (31).

To trigger neutralizing antibodies using recombinant Salmonella, it is essential that the antigen retains its native conformation. For HPV, this requires that the L1 proteins form VLPs. Papilloma VLPs have been shown to assemble in eucaryotic cells (15,22,45,48,61), but not in prokaryotes. In bacteria mainly L1-fusion proteins were expressed (2,20, 24) and when bona fide L1 proteins were expressed, VLP assembly was not examined (11). As shown in this paper, HPV16 VLP assemble in Salmonella probably because the level of expression achieved in our experiments was high and capsid assembly does not require glycosylation (60). Capsid production in bacteria has also been reported for other viruses such as the nucleocapsid of Hepatitis B virus (52) and the capsid of Polyomavirus (30,46). Polyomavirus VP1 major capsid protein, analogous to HPV L1, forms capsomers when expressed in *E. coli* which subsequently self-assembled into VLPs in vitro (46). The fact that only capsomers but no VLPs were recovered is probably due to the reducing agents present during purification, which are known to disrupt capsids (47).

Nasal immunization with the PhoP$^c$/HPV strain induced systemic and mucosal antibodies against native but not denatured HPV16 VLPs. In contrast, recombinant vaccinia expressing HPV1 capsid protein triggered serum antibodies recognizing both folded and unfolded VLP, probably reflecting different mode of viral protein expression, and low PWV-specific genital IgA antibody titers (14), as expected with a non-mucosal route of immunization.

Antibody titers against the foreign antigen induced by PhoP$^c$/HPV compared to PhoP$^c$/HBc Salmonella were about 10 times lower (18). This could reflect differences in immunogenicity between the two viral antigens (51) or, more likely, differences in plasmid stability. In contrast to the HBc DNA, the plasmid carrying the HPV16-L1 DNA was unstable in Salmonella in vivo in the absence of selective pressure, since less than 1% of the Salmonella recovered from different tissues two weeks after immunization still harboured the L1 -containing plasmid (data not shown). To increase the stability of the plasmid we are currently recloning the L1 gene in β-aspartate semialdehyde dehydrogenase (asd)-based vectors which maintain selective pressure in vivo (36,56).

The above work also demonstrates the following points:

(a) that purified VLPs and Salmonella/HPV strains are capable of providing tumour protection in a HPV16 mouse tumour model.

(b) that chimeras of a HPV protein and a fission partner assemble in prokaryotes to form VLPs.

(c) that high levels of expression of HPV proteins that assemble to form VLPs can be obtained in *E. coli,* demonstrating hat the invention is applicable in prokaryotes other than Salmonella.

In conclusion, we have constructed a recombinant Salmonella strain expressing HPV 16-L1 capsid proteins and assembling VLPs that induce conformational serum IgG and vaginal sIgA antibodies recognizing VLPs. Neutralizing activities of these antibodies were tested and shown to display strong neutralizing activity in an HPV16(BPV1) infectivity assay.

TABLE 1

Titers of IgG (in serum) or IgA (in vaginal washes) against native and unfolded HPV16 VLP in mice immunized with PhoP$^c$/HPV

| Samples | anti-HPV16 VLP | HPV16 VLP | anti-unfolded[a] |
|---|---|---|---|
| | IgG titers[b] | | |
| #4 serum$_{(week\ 27)}$ | 60,000 | 100 | |
| #5 serum$_{(week\ 27)}$ | 80,000 | 200 | |
| #6 serum$_{(week\ 27)}$ | 20,000 | 100 | |
| Camvir[c] | 16,000 | | 80,000 |
| | IgA titers | | |
| #4 Vaginal Washes$_{(week\ 19)}$ | 40 | <1 | |
| #5 Vaginal Washes$_{(week\ 19)}$ | 20 | <1 | |
| #6 Vaginal Washes$_{(week\ 19)}$ | 40 | 1 | |

[a]ELISA plates were coated with VLP in Carbonate buffer pH 9.5
[b]Titers are expressed as the reciprocal of the highest sample dilution that yielded an OD$_{492}$ four times that of preimmune sample
[c]Anti-HPV16 L1 monoclonal IgG (35 μg/ml), 30) used as positive control References:

The references mentioned herein are all incorporated by reference.
1. Aggarwal et al, 1990. J. Exp. Med. 172(4):1083–90.
2. Banks et al, 1987J. Gen. Virol.
3. Borysievwicz et al, 1996. Lancet. 347(9014):1523–1527.
4. Breitburd et al,1995. J. Virol. 69:3959–3963.
5. Broker and Botchan.1986. Cancer Cells. 4:17–36.
6. Chen et al, 1992. J. Immunol. 148(8):2617–21.
7. Chen et al, 1991. Proc. Nat. Acad. Sci. USA. 88(1):110–4.
8. Chistensen and Kreider, 1990. J. Virol. 64(7):3151–6.
9. Connor and Stem, 1990. Int J. Cancer. 46(6):1029–34.
10. Curtiss, 1990. Attenuated Salmonella stains as live vectors for the expression of foreign antigens. Marcel Dekker, Inc., New York.
11. Davies et al, 1990. J. Gen. Virol.
12. Feltkamp et al, 1995. Eur. J. Immunol. 25(9):2638–2642.
13. Feltkamp et al, 1993. Eur. J. Immunol. 23(9):2242–9.
14. Hagensee et al, 1995. Virology. 206:174–182.
15. Hagensee et al, 1993 J. Virol. 67:315–322.
16. Hess et al, 1996. Proc. Nat. Acad. Sci. USA 93(4):1458–1463.
17. Holt et al, 1994.J. Immunol.153(1):256–61.
18. Hopkins et al, 1995. Inf. Imm. 63:3279–3286.
19. Howley, 1990. Papillomaviridae and their replication. Fields virology Raven press, New York.
20. Jenson et al, 1990. J. Inf. Dis.162(1):60–9.
21. Jenson et al, 1987Obst. Gynec. Clin. North Am.14(2):397–406.
22. Kimbauer et al, 1992. Proc. Nat. Acad. Sci. USA. 89:12180–12184.
23. Kirnbauer et al, 1993. J. Virol. 67:6929–6936.
24. Kochel et al, 1991. Virology.182(2):644–54.
25. Kuper et al, 1992. Immunol. Today.13:219–224.
26. Kutteh et al, 1990. Fert. Ster. 54(1):51–5.
27. Kutteh et al, 1988. Obst. and Gyn. 71:56–60.
28. Kutteh and Mestecky, 1994. Am. J. Reprod. Immunol. 31:40–46.
29. Lambert, 1991. J. Virol. 65(7):3417–20.
30. Leavit et al, 1985. J. Biol. Chem. 260(23):12803–9.
31. Londono et al, 1996. Vaccine.14(6):545–552.
32. McDermott and Bienenstock, 1979. J. Immunol.122:1892–1898.
33. McLean et al, 1990. J. Clin. Path. 43(6):488–92.
34. Meneguzzi et al, 1991. Virology.181(1):62–9.
35. Miller and Mekalanos, 1990. J. Bacteriol.172:2485–2489.
36. Nakayama et al, 1988. Biotechnol. 6:693–697.
37. Nardelli-Haefliger et al, 1996. Oral and rectal immunization of adult female volunteers with a recombinant attenuated *Salmonella typhi* vaccine strain. submitted.
38. Neutra et al, 1996. Ann. Rev. Immunol.14(275):275–300.
39. O'Reilly et al, 1992. Baculovirus Expression Vectors. A Laboratory Manual. Frerman W. H. and Company, New York.
40. Pfister, 1987Obst. Gynecol Clin North Am.14:349–361.
41. Roberts et al, 1994. Salmonella as Carriers of Heterologous Antigens, p. 27–58. CRC Press Inc.
42. Roden et al, 1995. J. Virol. 69:5147–5151.
43. Roden et al, 1996. J. Virol.in press.
44. Roden et al, 1996. J. Virol. 70:3298–3301.
45. Rose et al, 1994. J. Gen. Virol. 75: 2075–2079.
46. Salunke et al, 1986. Cell. 46(6):895–904.
47. Sapp et al, 1995. J. Gen. Virol.
48. Sasagawa et al, 1995. Virology. 206:126–135.
49. Schiffman et al, 1993. S. Nat. Cancer Inst,. 85(12):958–64.

50. Schödel, 1990. Sem. Immunol. 2:in press.
51. Schödel et al, 1990. Colloque Inserm ed, vol.194. John Libbey Eurotext, Montrouge.
52. Schödel et al, 1990a. J. Immunol.145(12):4317–4321
53. Schödel et al, 1993. Hybrid hepatitis B virus core/pre-S particles- position effects on immunogenicity of heterologous epitopes and expression in avirulent Salmonellae for oral vaccination. Plenum Press, New York.
54. Schödel et al, 1993. J. Biol. Chem. 268:1332–1337
55. Sminia et al, 1989. Crit. Rev. Immunol. 9:119–145.
56. Srinivasan et al, 1995. Biol. Reprod. 53(2):462471.
57 Suzich et al, 1995. Proc. Nat. Acad. Sci. USA. 92(25):11553–11557.
58. Sztein et al, 1995. J. Inmunol.155(8):3987–93.
59. Tindle et al, 1994. CuWr. Top. in Micr. Immunol.186 (217):217–53.
60. Zhou et al, 1993. Virology.194:210–218.
61. Zhou et al, 1991. Virology.185:251–257.
62. zur Hausen and Schneider, 1987. The role of papillomaviruses in human anogenital cancer, in The papoviviridae: the papillomaviruses, vol. 2. Salzman, N. P. and Howley, P. M. eds, Plenum, New York.
63. Bartolomeusz et al, 1990. Immunology. 69–190–194.
64. Bartholomeusz et al, 1986. Journal of Gastroenterology and Hepatology.1:61–67
65. Curtiss et al, 1990. Res. Microbiol.141(7–8):797–806.
66. Curtiss et al, 1994. Nonrecombinant and recombinant avirulent Salmonella Vacines. In G. P. e. a. Talwar (ed.), Recombinant and Synthetic Vaccines. Narosa Publishing House, New Delhi, India.
67. Curtiss and Kefly, 1987 Infect. Irrmiun. 55(12):3035–3043.
68. Curtiss et al, 1994. Recombinant Salmonella Vectors in Vaccine Development, p. 23–33. In F. Brown (ed.), Recombinant Vectors in Vaccine Development, vol. 82. Karger, Basel.
69. Curtiss et al, 1989. Immunol. Invest.18(14):583–596.
70. Ferreccio et al, 1989. Journal of Infectious Diseases.159 (4):766–9.
71. Forrest et al, 1990. Vaccine. 8:209–212.
72. Germanier and Firer, 1975. J. Infect. Dis.131(5):553–558.
73. Hone et al, 1992. Journal of Clinical Investigation. 90(2):412–20.
74. Kelly et al, 1992. Infect. Immun. 60(11):4881–4890.
75. Roberts et al, 1994. Salmonella as Carers of Heterologous Antigens, p. 27–58. CRC Press Inc.
76. Schödel, 1992. Adv. Vir. Res. 41:409–446.
77. Schödel ct al, 1996. Hybrid Hepatitis B virus Core Antigen as a Vaccine Carier Moiety: II Expression in avirulent Salmonella .spp . for Mucosal immunization, p.15–21. In S. Cohen and A. Shafferman (ed.), Novel Strategies in Design and Production of Vaccines. Plenum Press, NY.
78. Silva et al, 1987 Journal of Infectious Diseases.155(5):1077–1078.
79. Tacket et al, 1992. Infection and Immunity. 60:536–541.
80. Tacket et al, 1992. Vaccine, 10: 443–446
81. Hohmann et al, 1996. J. Inf. Dis., 174:1408–1414.
82. Campo et al, 1993. Journal of General Virology, 74:945–953.
83. Chen et al, 1992. J. Immunol., 148(8):2617–21.
84. Greestone et al, 1997 HPV16 L1/L2-E7 Chimeric papillomavirus-like particles induce both neutralizing antibodies and E7 specific anti-tumour immunity. 16th International Papillomavirus Conference, Siena, Italy, Abstract:177.
85. Lin et al, 1996. Cancer Research, 56(1):21–26.
86. Nardelli-Haefliger et al, 1997 Infection and Immunity, 65(8):3328–3336.
87. Vandriel et al, 1996. Annals of Medicine, 28(6):471–477.
88. Galan, Nakayama and Curtiss (1990) Gene 94:29–35.
89. Nakayama, Kelly and Curtiss (1988) Biotechnol. 6:693–697

What is claimed is:

1. An attenuated strain of a prokaryotic microorganism, the attenuated microorganism strain being an attenuated strain of Salmonella suitable for therapeutic treatment of a human or animal body, wherein the microorganism is transformed with nucleic acid encoding Human papillomavirus 16 L1 major capsid protein wherein the protein assembles in the microorganism to form virus like particles (VLPs) that are capable of eliciting an immune response sufficient to produce neutralizing antibodies in serum and/or genital secretions when the microorganism is administered to said human or animal body.

2. The attenuated microorganism strain of claim 1 which is an attenuated strain of *Salmonella tyghimurium, Salmonella typhi, Salmonella dublin,* or *Salmonella enteretidis.*

3. The attenuated microorganism strain of claim 2 wherein the Salmonella strain is attenuated by mutation selected from the group consisting of mutation in the PhoP/PhoQ system and Δcya. Δcyp and Δcdt mutation.

4. The attenuated microorganism strain of claim 1 wherein the papillomavirus virus major capsid protein is expressed as a chimera with a fusion partner.

5. The attenuated microorganism strain of claim 4, wherein the papillomavirus major capsid protein is coexpressed with L2 protein, the L2 protein being fused to the fusion partner.

6. The attenuated microorganism strain of claim 4 wherein the fusion partner is E6, E7 or E2 HPV protein, an immunogenic protein from a non-HPV pathogen or a tumour specific antigen.

7. The attenuated microorganism strain of claim 1 wherein the microorganism is transformed with nucleic acid encoding two or more papillomavirus virus major capsid proteins.

8. A composition comprising one or more of the attenuated microorganisms of claim 1, in combination with a physiologically acceptable carrier.

9. A vaccine comprising one or more of the attenuated microorganisms of claims 1, in combination with a physiologically acceptable carrier.

10. The vaccine of claim 9 formulated for mucosal immunization.

11. The vaccine of claim 10 wherein the mucosal immunization is via oral, rectal, nasal, or genital routes.

12. The vaccine of claim 9 wherein the vaccine provides protection against Human papillomavirus 16 infection or Human papillomavirus 16 associated cancer of the anogenital tract.

13. A method for producing assembled papillomavirus virus like particles comprising culturing an attenuated microorganism strain of claim 1 and recovering the assembled virus like particles thus produced.

14. A method of detecting the presence of anti-papillomavirus antibodies in a sample from a subject, the method comprising immobilizing the HPV VLPs on a solid support, exposing the support to the sample and detecting the antibodies binding to the immobilized HPV VLPs, wherein the HPV VLPs are produced by an attenuated microorganism strain of claim 1.

15. A method of treating a patient in need of prophylaxis or therapy of a Human papillomavirus 16 infection or Human papillomavirus 12 infection associated cancer of the anogenital tract comprising administering to that patient a therapeutically effective amount of an attenuated microorganism as claimed in claim 1.

16. A method as claimed in claim 15 wherein the microorganism is a Δ β-aspartate semi-aldehyde dehydrogenase (asd) attenuated Salmonella including a plasmid carrying both asd and Human papillomavirus 16 L1 major capsid protein encoding nucleic acid sequences such that an in vivo selection pressure is provided to maintain the presence in the microorganism of the Human papillomavirus 16 L1 major capsid protein encoding DNA.

* * * * *